(12) United States Patent
Allain et al.

(10) Patent No.: US 10,353,069 B2
(45) Date of Patent: Jul. 16, 2019

(54) ULTRASOUND IMAGING SYSTEM WITH IMAGE RATE SEQUENCES

(75) Inventors: Pascal Allain, Eindhoven (NL); Olivier Gerard, Eindhoven (NL); Karl Thiele, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 1520 days.

(21) Appl. No.: 12/376,308

(22) PCT Filed: Aug. 3, 2007

(86) PCT No.: PCT/IB2007/053062
§ 371 (c)(1),
(2), (4) Date: May 13, 2009

(87) PCT Pub. No.: WO2008/017994
PCT Pub. Date: Feb. 14, 2008

(65) Prior Publication Data
US 2010/0228127 A1 Sep. 9, 2010

(30) Foreign Application Priority Data

Aug. 9, 2006 (EP) ..................................... 06300867

(51) Int. Cl.
*A61B 8/00* (2006.01)
*A61B 8/08* (2006.01)
(Continued)

(52) U.S. Cl.
CPC ............ *G01S 15/8993* (2013.01); *A61B 8/08* (2013.01); *A61B 8/0883* (2013.01); *A61B 8/483* (2013.01);
(Continued)

(58) Field of Classification Search
CPC ............. G01S 15/8993; G01S 7/52087; G01S 7/52085; G01S 7/52071; G01S 7/52063;
(Continued)

(56) References Cited

U.S. PATENT DOCUMENTS 5,615,680 A   4/1997 Sano
5,993,390 A   11/1999 Savord et al.
(Continued)

FOREIGN PATENT DOCUMENTS

EP   1542165 A1   6/2005
EP   1685799 A1   8/2006

OTHER PUBLICATIONS

Shinji Tsuruoka, et al; Regional Wall Motion Tracking System for High-Frame Rate Ultrasound Echocardiography, Proceedings of 4th International Workshop on Advanced Motion Control, AMC '96—MIE, Mar. 18-21, 1996 IEEE, vol. 1, pp. 389-394 ISBN; 07803-3219-9.

(Continued)

*Primary Examiner* — Serkan Akar

(57) ABSTRACT

An ultrasonic diagnostic imaging system is described by which a first sequence of ultrasound images of an organ such as the heart is acquired at a first image acquisition rate. The first sequence preferably images a larger volume or area in which a region of interest is located. Then a second sequence of three-dimensional ultrasound images of a sub-volume covering a part of anatomy of interest in the first sequence is acquired at a second image acquisition rate which is greater than the first acquisition rate. A third sequence of three-dimensional ultrasound images of a reference sub-volume is acquired at the second image rate. The second and third sequences of three-dimensional images are compared, (Continued)

enabling a clinician to focus on synchronism defects in the anatomy of interest with more precision and with a faster acquisition time.

16 Claims, 12 Drawing Sheets

(51) Int. Cl.
    *G01S 7/52*     (2006.01)
    *A61B 8/14*     (2006.01)
    *G01S 15/89*     (2006.01)

(52) U.S. Cl.
    CPC .......... *A61B 8/488* (2013.01); *G01S 7/52071* (2013.01); *G01S 7/52085* (2013.01); *G01S 7/52087* (2013.01); *A61B 8/543* (2013.01); *G01S 7/52063* (2013.01)

(58) Field of Classification Search
    CPC ........... A61B 8/08; A61B 8/488; A61B 8/483; A61B 8/0883; A61B 8/543
    USPC .................................. 600/437, 443, 444, 447
    See application file for complete search history.

(56) References Cited

U.S. PATENT DOCUMENTS

| | | | |
|---|---|---|---|
| 6,139,500 A * | 10/2000 | Clark ........................ | A61B 8/08 128/916 |
| 6,159,153 A * | 12/2000 | Dubberstein ............ | A61B 8/06 128/916 |
| 6,547,735 B1 * | 4/2003 | Henderson ............... | A61B 8/14 128/916 |
| 7,043,063 B1 * | 5/2006 | Noble et al. ................... | 382/128 |
| 2003/0006984 A1 * | 1/2003 | Gerard et al. ................ | 382/154 |
| 2003/0216644 A1 * | 11/2003 | Hall ......................... | A61B 8/06 600/437 |
| 2004/0122319 A1 * | 6/2004 | Mehi .................... | G01S 7/52034 600/443 |
| 2004/0193042 A1 * | 9/2004 | Scampini et al. ............ | 600/437 |
| 2004/0254486 A1 | 12/2004 | Heimdal | |
| 2005/0033123 A1 | 2/2005 | Gardner et al. | |
| 2005/0113689 A1 | 5/2005 | Gritzky | |
| 2005/0113690 A1 | 5/2005 | Halmann et al. | |
| 2005/0228276 A1 | 10/2005 | He et al. | |
| 2006/0034513 A1 * | 2/2006 | Cai et al. ...................... | 382/173 |
| 2006/0045328 A1 * | 3/2006 | Jacob ..................... | G06T 17/00 382/154 |
| 2006/0182320 A1 * | 8/2006 | Peszynski ............ | A61B 8/0833 382/128 |
| 2007/0123110 A1 * | 5/2007 | Schwartz ................ | A61B 8/14 439/638 |

OTHER PUBLICATIONS

"Standardized Myocardial Segmentation and Nomenclature for Tomographic Imaging off the Heart" The Cardic Imaging Committee of The Council on Clinical Cardiology of The American Heart Association, 2002;105;539-542.

* cited by examiner

ULTRASOUND IMAGING SYSTEM WITH IMAGE RATE SEQUENCES

FIELD OF THE INVENTION

The present invention relates to an ultrasound imaging system, and to a corresponding method.

BACKGROUND OF THE INVENTION

A medical ultrasound imaging system is disclosed in U.S. Pat. No. 5,993,390 which makes it possible to acquire a three dimensional image of an organ. In the example disclosed, the organ is the heart. Such a system cooperates with a matrix of more than a thousand of piezoelectric elements with associated coaxial cables, which are called transducers forming a transducer's array, the transducers allowing to send ultrasound scan lines through the organ. It means that a piezoelectric element allows to transmit an ultrasound pulse, to receive a pressure wave and to convert it into an electrical signal. A scan line is composed of a plurality of electrical signals coming from the piezo-electric elements. This transducer's array and its electronics form an ultrasonic probe which is applied onto a patient body near the organ to be imaged. Hence, an ultrasound image is based upon all the ultrasound scan lines and interpolations between said scan lines, both allowing a definition of said image in different gray levels. The 3D images are usually used to detect a defect on the organ.

One drawback of said imaging system is that, in order to check an entire organ such as the left ventricle of the heart, with a good image quality, the 3D image rate is low because of the laws of physics governing the acquisition, in particular the speed of sound of 1540 m/sec. Typically, the image rate is around 20 Hz (that means only twenty images per second). Indeed, the image acquisition rate is function of:

The field of view,
The number of scan lines,
The scan lines density, and
The depth of the image.

In order to decrease the time of acquisition, and thus to increase the image rate, one can decrease the number of scan lines or decrease the scan lines density. But unfortunately, this solution leads to a very low resolution of the image. It is therefore difficult to detect any defect on the organ via the use of the 3D ultrasound image at high image rate.

SUMMARY OF THE INVENTION

It is an object of the invention to propose an ultrasound imaging system which allows ultrasound 3D images acquisition of an organ with a good image resolution in order to detect a synchronism defect between different parts of the organ.

To this end, the ultrasound imaging system comprises:
A controller for controlling the following operations:
Acquisition at a first image rate of a first sequence of ultrasound images of an organ,
Acquisition at a second image rate of a second sequence of ultrasound three-dimensional images of a sub-volume covering a part of interest in said first sequence,
Acquisition at the second image rate of a third sequence of ultrasound three-dimensional images of a reference sub-volume, and
A comparator for comparing said second and third sequences of three-dimensional images.

Hence, thanks to the images acquisition at two different image rates, one can first look for a part of said organ which can be interesting, and one can subsequently focus on said part with more precision and within a faster time acquisition. As a whole view of said part is available at high image rate, it is easier to quantify a synchronism defect as the quality of image is increased.

According to a not limited embodiment, the second image rate is equal to or higher than 50 Hz. It allows to focus on the sub-volumes with a very good spatial and temporal resolution which lead to a good quality of 3D image.

In a first embodiment, the images acquired during the first step at the first image rate are in two-dimensions. In this case, the first image rate may be higher than or equal to 40 Hz. It allows to have a large field of view of the organ.

In a second embodiment, the images acquired during the first step at the first image rate are in three-dimensions. It allows to have a more precise view of the part of the organ which is interesting.

According to a not limited embodiment, the system further comprises means for enabling selection of said part of interest in said first sequence of ultrasound images. It makes it possible to make an automatic selection or to help a user in selection of a part of interest.

According to a first variant of selection, the means for enabling selection of the part of interest are arranged to enable a selection based upon velocity information of some parts of the organ.

It allows to make a quantitative detection of the part of interest.

According to a second variant of selection, the means for enabling selection of the part of interest, are arranged to enable a selection based upon a COLOR KINESIS method. COLOR KINESIS is a registered trademark of Koninklijke Philips Electronics N.V.

According to a not limited embodiment of an acquisition of images, the controller is arranged to control acquisition of a plurality of sequence of images in a plurality of planes during a same time period. It allows obtaining an image of portions of lot of segments of the inner wall of the organ when the organ is represented by segments.

The present invention also relates to a method for ultrasound imaging which comprises the steps of:
Acquiring at a first image rate a first sequence of ultrasound images of an organ,
Acquiring at a second image rate a second sequence of ultrasound three-dimensional images of a sub-volume covering a part of interest in said first sequence,
Acquiring at the second image rate a third sequence of ultrasound three-dimensional images of a reference sub-volume,
Comparing said second and third sequences of three-dimensional images.

According to a not limited embodiment, the method further comprises a step of selecting the part of interest.

According to a first variant of selection, the step of selecting comprises:
a step of acquiring velocity information of some parts of the organ,
a step of colorization of these velocity information, and
a step of visual assessment of a part of the organ whose color is not uniform with the other parts.

It allows to make a qualitative detection of the part of interest.

According to a second variant of selection, the step of selecting comprises:

a step of acquiring velocity curves associated to some parts of the organ, and a step of visual assessment of a delay between these velocity curves at a representative time.

It allows to make a qualitative detection of the part of interest.

The present invention finally relates to a computer program product comprising program instructions for implementing said method.

These and other aspects of the invention will be apparent from and will be elucidated with reference to the embodiments described hereinafter.

BRIEF DESCRIPTION OF THE DRAWINGS

The present invention will now be described in more detail, by way of not limited examples, with reference to the accompanying drawings, wherein.

DETAILED DESCRIPTION OF THE INVENTION

The ultrasound imaging system SYS can be used to acquire images of any organ such as the heart. The example of a heart HRT will be considered in the following description, and more precisely the left ventricle of the heart.

Figure 1:
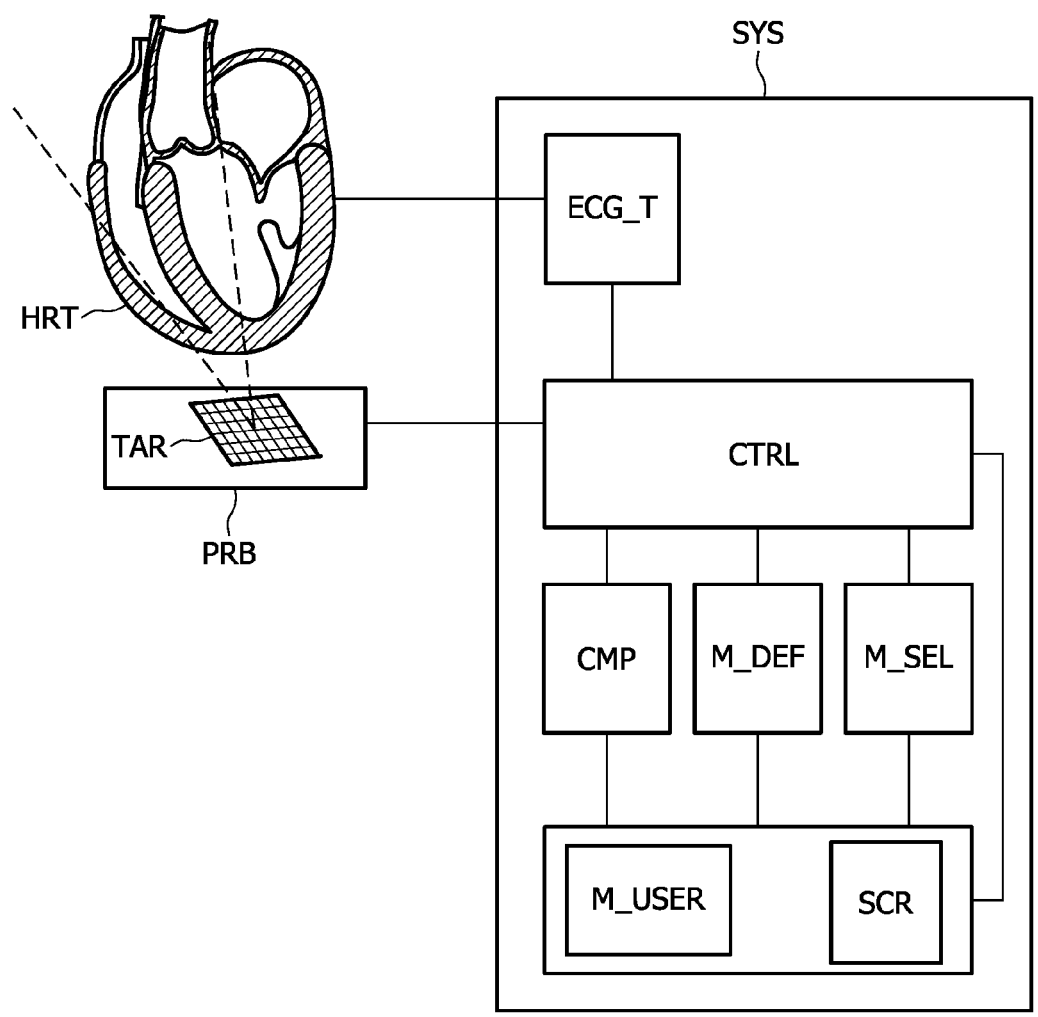
FIG. 1 is a schematic diagram of the ultrasound imaging system according to the present invention which cooperates with an ultrasonic probe.

The ultrasound imaging system SYS is described in FIG. 1.

It cooperates with a transducer's array TAR and its associated electronics, the whole forming an ultrasonic probe PRB.

The system SYS comprises:

A controller CTRL for controlling acquisition of a sequence of images via said ultrasonic probe PRB. This controller CTRL makes it possible to change the image rate acquisition, and to configure the piezoelectric elements of the transducer's array TAR in order to perform the following operations:

Acquisition of a first sequence of ultrasound images I1 of an organ at a first image rate IR1, Acquisition at a second image rate IR2 of a second sequence of ultrasound three-dimensional images of a sub-volume S_V1 covering a part of interest RI/VI in said first sequence I1, Acquisition of a third sequence of ultrasound three-dimensional images of a reference sub-volume S_V0 at the second image rate IR2, A comparator CMP for comparing said first sub-volume S_V1 with said reference sub-volume S_V0 based upon the three-dimensional images sequences, A screen SCR for displaying the sequences of ultrasound images acquired, such as a LCD screen, and A user interface M_USER.

It is to be noted that the controller CTRL comprises a microprocessor that can be preprogrammed by means of instructions or that can be programmed by a user of the system SYS via the interface M_USER.

In a not limited embodiment, the ultrasound imaging system SYS further comprises:

Means M_SEL for enabling selection of the part of interest RI/VI within said first sequence of images I1, Means M_DEF for determining the first sub-volume S_V1 covering said part of interest RI/VI and for determining the reference sub-volume S_V0.

Figure 2:
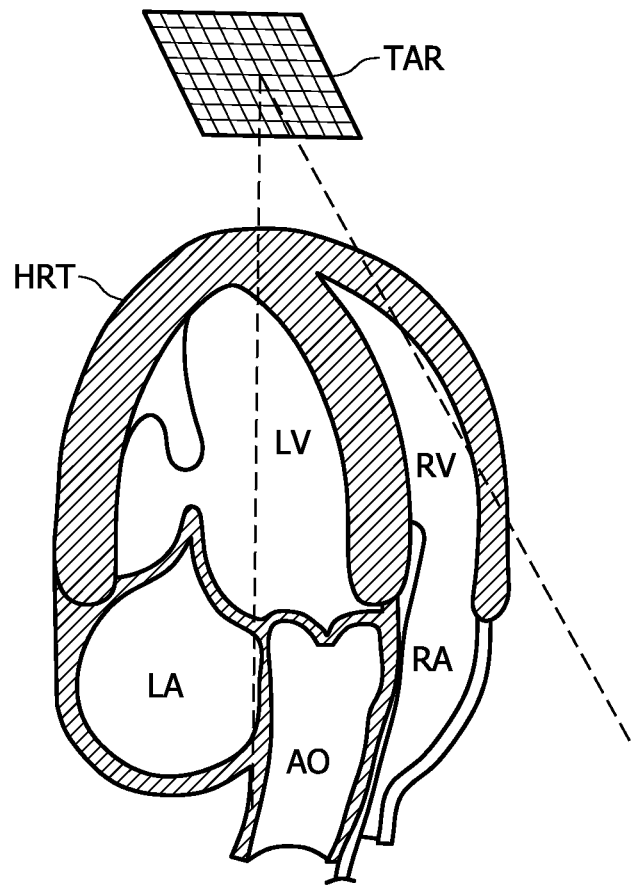
FIG. 2 is a schematic drawing of an organ such as the heart, from which a sequence of images is acquired via the ultrasound imaging system of FIG. 1.

One reminds that a heart HRT is composed of a left and a right ventricles LV and RV, an aorta AO, and a left and right atrium LA and RA as shown in FIG. 2, and that the arterial blood goes from the left ventricle LV to the aorta AO while the right ventricle RV exits the venous blood received from the right atrium RA to the pulmonary artery. As the way the left ventricle LV is working is indicative of the health of the heart HRT, one focus more particularly on said left ventricle LV when using the ultrasound imaging system SYS.

Figure 3:
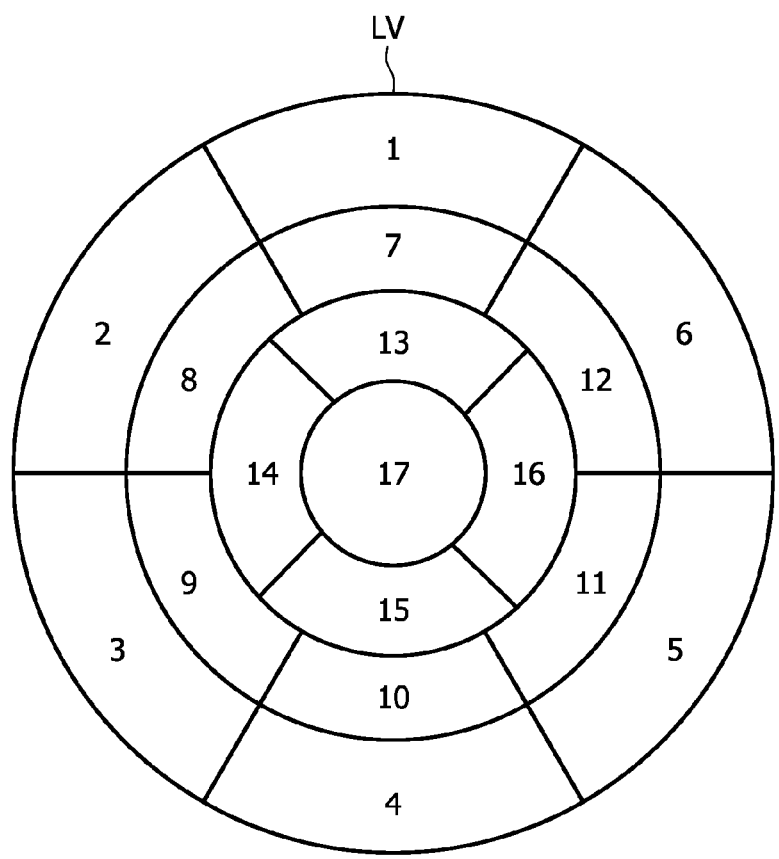
FIG. 3 is a first view of a segmentation of an organ such as the left ventricle of the heart, used by the ultrasound imaging system of FIG. 1.
Figure 4:
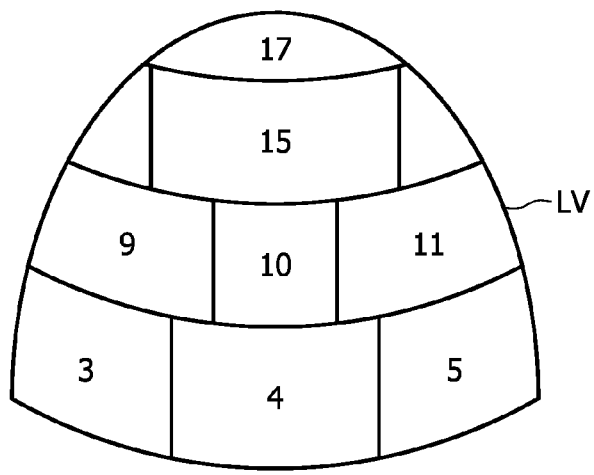
FIG. 4 is a second view of a segmentation of an organ such as the left ventricle of the heart, used by the ultrasound imaging system of FIG. 1.
Figure 5:
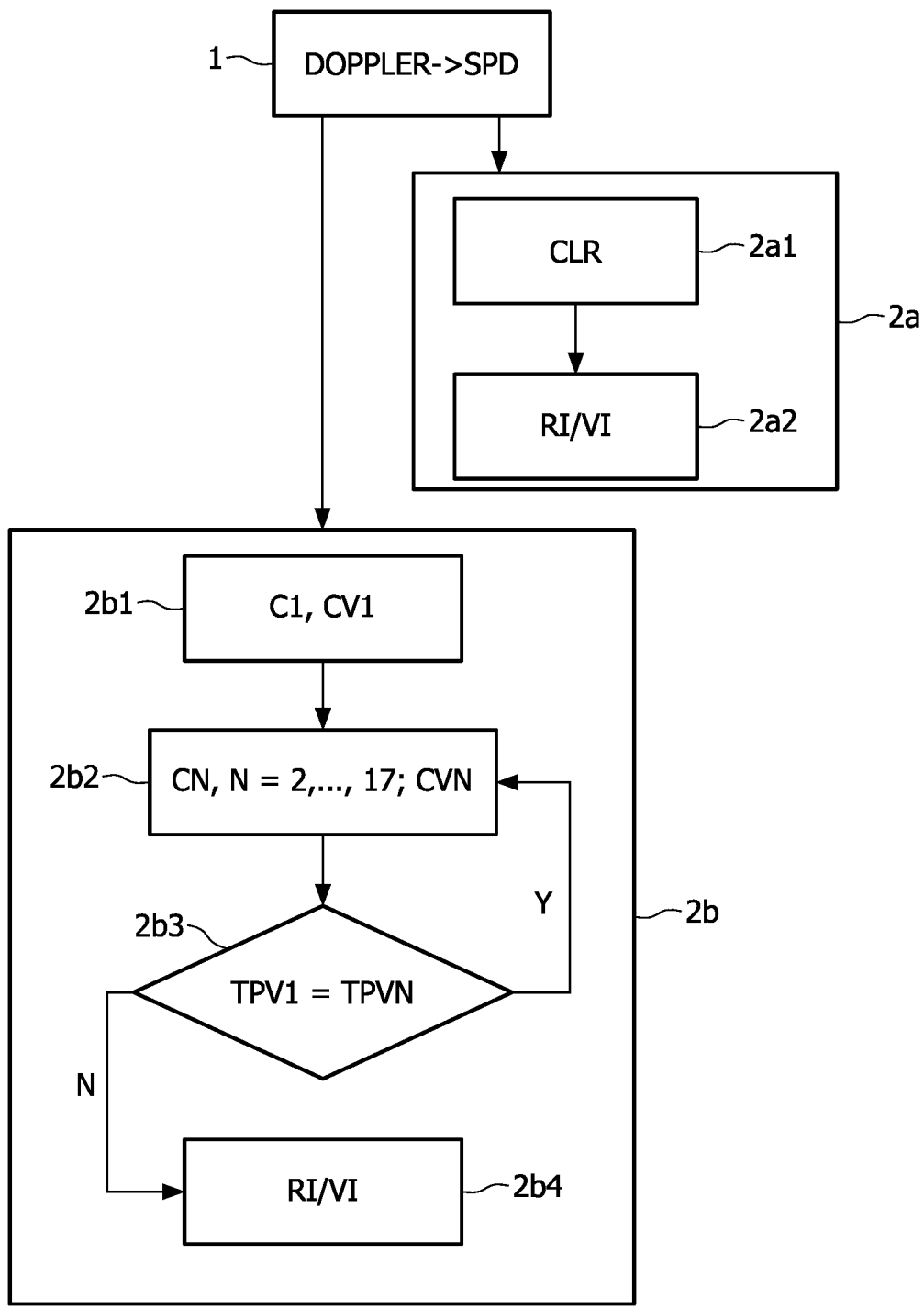
FIG. 5 represents a first variant of images acquisition by means of the ultrasound imaging system of FIG. 1.

Referring now to FIG. 3, the inner wall of left ventricle LV of the heart HRT is segmented in seventeen segments SG as defined in the standard "Standardized Myocardial Segmentation and Nomenclature for Tomographic Imaging of the Heart" by the Cardiac Imaging Committee of the Council on Clinical Cardiology of the American Heart Association. Thus, FIG. 3 is a display on a circumferential polar plot of such a segmentation and FIG. 4 is a 3D view of such segmentation. The seventeen segments are named by the standard. For example, the segment number 17 is the apex, and the segments number 1 and 7 which identify the locations of the anterior wall at the base and mid-cavity are named basal anterior and mid-anterior. Such a segmentation may be used by the ultrasound imaging system as described below.

It should be noted that in the present application, the left ventricle LV of the heart HRT is in itself considered as an organ.

In order to acquire images of a heart HRT, the ultrasonic probe PRB is applied on the body of a patient, at the apex near the heart in a not limited embodiment, and the ultrasound imaging system SYS performs the operations described hereinafter.

1) Acquisition of a first sequence of ultrasound images I1 of the heart HRT, more particularly of the left ventricle LV, at a first image rate IR1. This image rate IR1 is chosen in order to have a large field of view so as to view the entire heart or at least the entire left ventricle LV.

In a first embodiment, the acquisition can be made in three-dimensions at a first image rate IR1 between 15 et 30 HZ. It is to be noted that if the image rate is lower, one can't see the image moving. This 3D acquisition allows obtaining a volume and then making some section in any plane. It is to be noted that in order to view the entire volume of the left ventricle LV, the images acquisition is performed during four cardiac cycles, wherein one fourth of the left ventricle LV is acquired at each cardiac cycle.

In a second embodiment, the acquisition can be made in two-dimensions at a first image rate IR1 higher than or equal to 40 Hz. In a not limited embodiment, this rate may be as high as 180 Hz, depending on the structure of the transducer's array TAR. This 2D acquisition is faster than the 3D acquisition but it is only done in a plane perpendicular to the transducer's array TAR.

In order for the user to choose between the 2D or 3D acquisition, the user interface M_USER comprises means for choosing between these two modes.

2) Selection of a region/volume of interest RI/VI.

According to a first variant, in a first step 1, one uses the tissue Doppler imaging method, well-known by the person skilled in the art, to acquire velocity information SPD of the segments of the left ventricle LV. The result is a sequence of velocity images of the segments when they move, for example, toward the transducer's array TAR.

In a second step 2a), and in a first embodiment of this first variant, firstly (2a1), a color CLR is associated to the velocity SPD of the segments of the heart HRT in order to be displayed on the screen SCR. For example, a red color can be used when the segments contract whereas a blue color can be used when the segments relax. When the heart is working correctly, the whole left ventricle LV should be displayed in red when it contracts, and in blue when it relaxes. If it is not the case, the left ventricle LV is displayed for some parts in red and for other parts in blue. The colors are not uniform. It means that some segments contract or relax later than other segments of the heart HRT because their speed peak are different.

Secondly (2a2), these segments which define some region/volume of interest RI/VI, are selected. This may be performed automatically by the means M_SEL for enabling selection.

It is to be noted that, of course, the automatic detection and selection of the region/volume RI/VI based on the difference of colors in a same phase (contraction or relaxation) can be replaced by a visual assessment. To this end, the user interface M_USER comprises means to let the user choose between the automatic and the visual detection/selection of a part of interest RI/VI. In this case the means M_SEL for enabling selection of a part of interest only comprise the means for acquiring the colored velocity images.

In a second step 2b), and in a second embodiment of this first variant, velocity curves are defined based on the velocity images.

Figure 6:
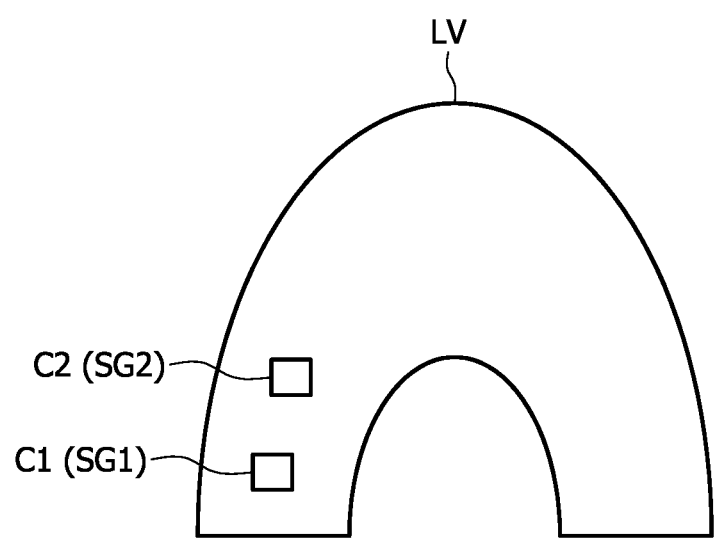
FIG. 6 is a schematic diagram of the left ventricle of the heart used when the variant of FIG. 5 is applied.
Figure 7:
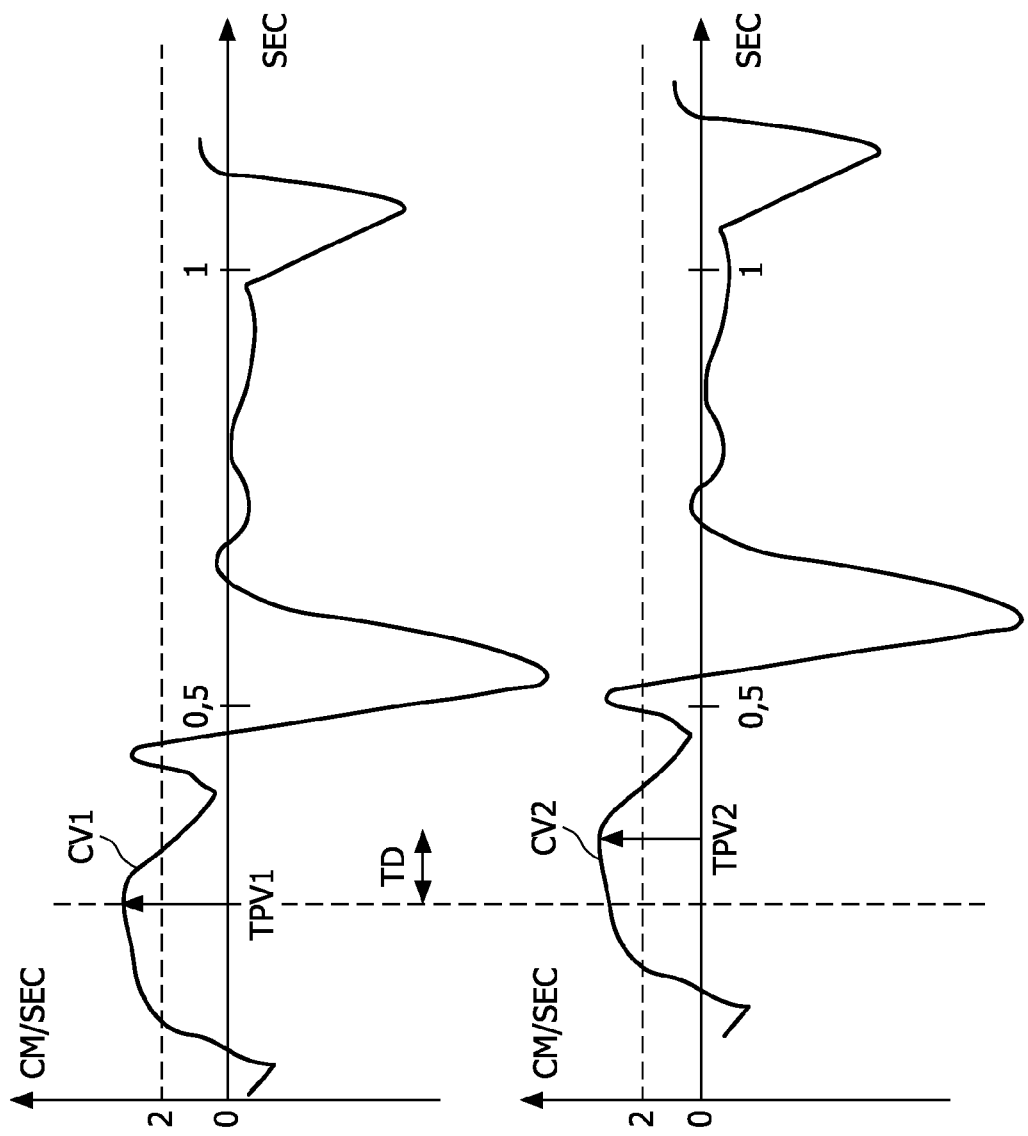
FIG. 7 shows two curves used within the variant of FIG. 5.

Firstly (sub-step 2b1), a cursor C is positioned on the image I1 displayed at a first position C1 corresponding to a first segment SG1 of the left ventricle LV, as illustrated in FIG. 6 where one slice of a volume V is represented (in the example of 3D image acquisition). A first curve CV1, as illustrated in FIG. 7, is defined based upon the velocity images. This curve represents the motion of a portion of the first segment SG1 of the left ventricle LV. As shown in FIG. 7, the X-axis represents the time and the Y-axis represents the speed of the motion (in centimeter per second).

Secondly (sub-step 2b2), the cursor C is positioned on the image I1 displayed at a second position C2 corresponding to a second segment SG2 of the heart HRT. A second curve of motion CV2, as illustrated in FIG. 7, is defined.

Thirdly (sub-step 2b3), one detects a representative time on the two curves CV1 and CV2, here in a not limited embodiment, a time to peak velocity TPV, which is the time at which the portion of a segment of the heart HRT moves the faster, and one compares the two times to peak velocity TPV1, TPV2, in order to detect a delay TD between these two times. In the example of FIG. 7, a delay TD is found between segment SG1 and segment SG2.

Finally (sub-step 2b4), if a delay TD superior to a predetermined threshold is detected, a region of interest RI (in the case of 2D images acquisition) or volume of interest VI (in the case of 3D images acquisition) to be further analyzed is selected.

If no delay is detected or the delay is too low, then the second and third sub-steps 2b2, 2b3 are repeated, until a delay between the first segment SG1 and another segment SGN is detected.

To this end, the second position C2 of the cursor C is changed and one repeats the second and further sub-steps until a delay is detected.

It is to be noted that more than two cursors can be used if wanted.

It is to be noted that, of course, the automatic detection of a delay between the two curves, and therefore the automatic selection of the region/volume of interest RI/VI can be replaced by a visual assessment. To this end, the user interface M_USER comprises means to let the user choose between the automatic and the visual selection. In this case the means for enabling selection of a part of interest only comprise the means for computing the curves CV1 and CV2.

Figure 8:
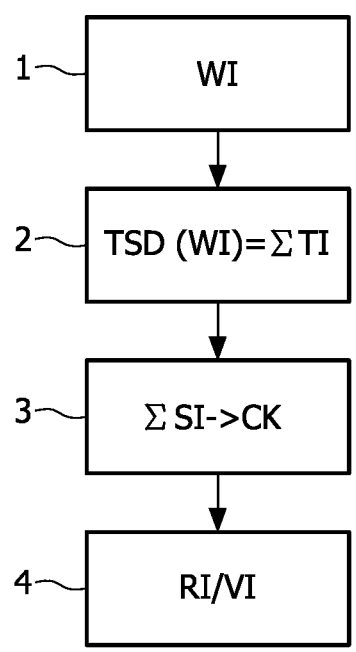
FIG. 8 represents a second variant of images acquisition by means of the ultrasound imaging system of FIG. 1.

According to a second variant, in a first step 1) illustrated in FIG. 8, after acquisition of the 2D or 3D sequences of images, one determines the inner wall WI of the left ventricle LV. This is done automatically, in a not limited example, by an acoustic quantification method well-known from the person skilled in the art.

Figure 9:
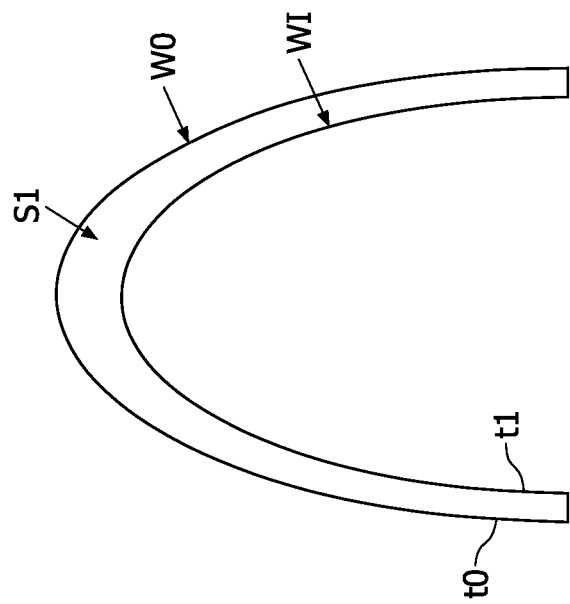
FIG. 9 is a first schematic diagram of the left ventricle of the heart with its walls used within the variant of FIG. 8.

In a second step 2), one follows the contraction of the inner wall WI during a period TSD representative of a systole phase. The inner wall WI and outer wall WO are illustrated in FIG. 9.

One reminds that the systole phase is a phase where the heart HRT contracts which leads to the ejection of the blood into the arteries, and the diastole phase is a phase where the heart HRT relaxes. In order to determine the systole phase, one uses an electrocardiogram ECG of the patient which shows the beginning and the end of the systole. Thus, the acquisition of the ultrasound images are synchronized on said electrocardiogram ECG. In order to make the synchronisation, the ultrasound imaging system SYS comprises an ECG trigger ECG_T.

This period TSD is a function of the images rate acquisition IR and can be divided in a number of predefined intervals TIn. This number of intervals depends on the heart rate and the image rate. During each interval TI, one can follow the motion of the inner wall WI from a first time ti to a second time ti+1 of an interval TI. In the example given in FIGS. 9 to 12, the first interval TI1 is defined by the two times t0 and t1, the second interval TI2 by the two times t1 and t2, . . . etc.

In case of a 2D image acquisition, the interval TI may for instance be equal to 10 ms which corresponds to an image rate IR1 of 100 Hz.

The interval will be lower in the case of a 3D image acquisition.

It is to be noted that the period TSD may also be the diastole phase.

In a third step 3), one defines a contour associated to each motion of the inner wall WI and which corresponds to each interval TI. In the example illustrated, five surfaces S1 to S5 are drawn, a surface being delimited by two contours. Then, the surfaces SI are colorized with a technique called the COLOR KINESIS method (CK) well-known by the person skilled in the art. It displays both the magnitude and timing of endocardial motion in real time. The COLOR KINESIS display superimposes a color overlay on a two dimensional echocardiographic image. The number of pixels represents the magnitude of endocardial motion, while the different colors represent the timing of endocardial motion according to a predefined color encoded map.

In a fourth step 4), thanks to the colors applied, the regions/volumes of the heart HRT which contracts correctly and the regions/volumes which do not can be differentiated. These later regions/volumes represent regions/volumes of interest RI/VI that can be selected.

Figure 10:
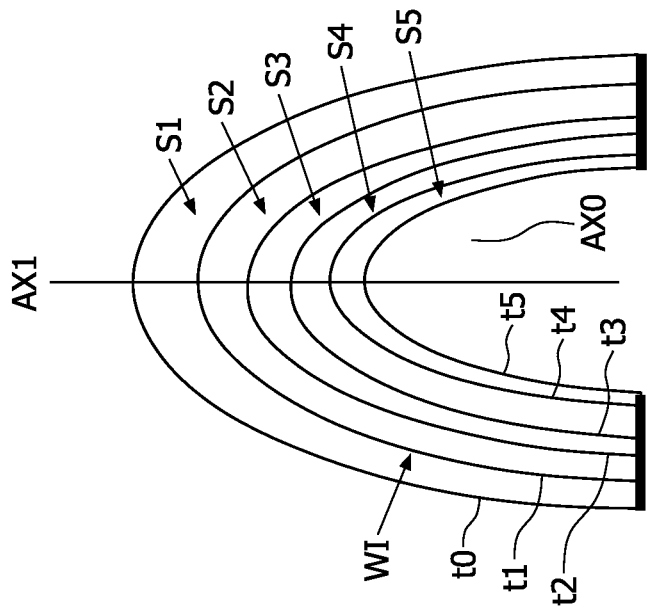
FIG. 10 is a second schematic diagram of the left ventricle of the heart with its walls used within the variant of FIG. 8.
Figure 12:
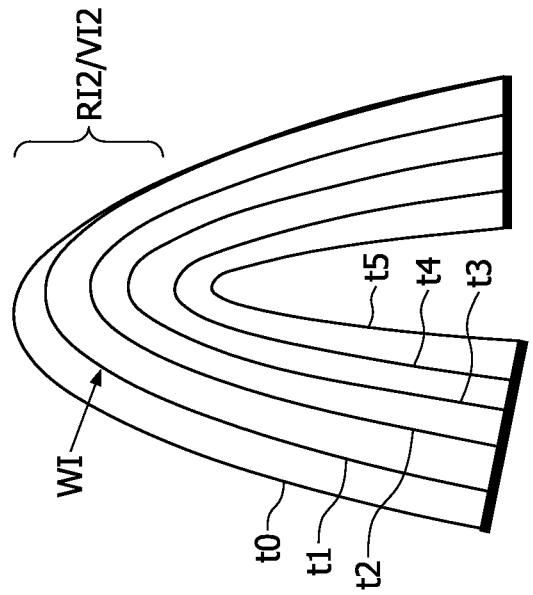
FIG. 12 is a fourth schematic diagram of the left ventricle of the heart with its walls used within the variant of FIG. 8.
Figure 11:
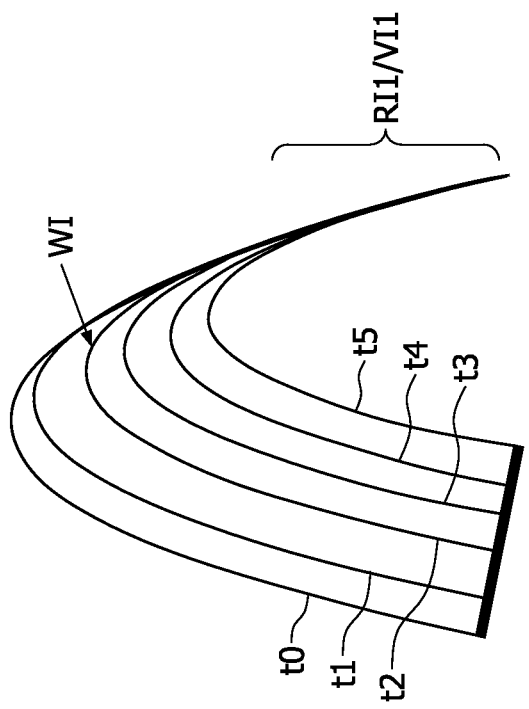
FIG. 11 is a third schematic diagram of the left ventricle of the heart with its walls used within the variant of FIG. 8.

In the examples of FIGS. 9 and 10, all the regions/volumes of the heart HRT contracts correctly, whereas in FIG. 11 a region/volume of interest RI1/VI1 of the heart HRT doesn't contract at all and in FIG. 12, a region/volume of interest RI2/VI2 of the heart HRT contracts with a delay.

It is to be noted that, of course, the automatic detection of a difference of colors, and therefore the automatic selection of the region/volume RI/VI can be replaced by a visual assessment. To this end, the user interface M_USER comprises means to let the user chose between the automatic and the visual selection.

In another embodiment (not represented) of this second variant, in the third step 3), one can also extract a velocity curve (as described in the first variant) of a segment of said inner wall WI, the displacement being taken perpendicular to the inner wall (for example axis AX0 as illustrated in FIG. 10) or toward the center of gravity of the LV, or toward a predefined axis (for example axis AX1 as illustrated in FIG. 10).

It is to be noted that an X-plane mode can be used in the acquisition operation at the first rate IR1 as explained below.

The X-Plane mode acquisition makes it possible to acquire sequences of images in a plurality of planes during a same time period, for example during a systole phase.

Figure 13:
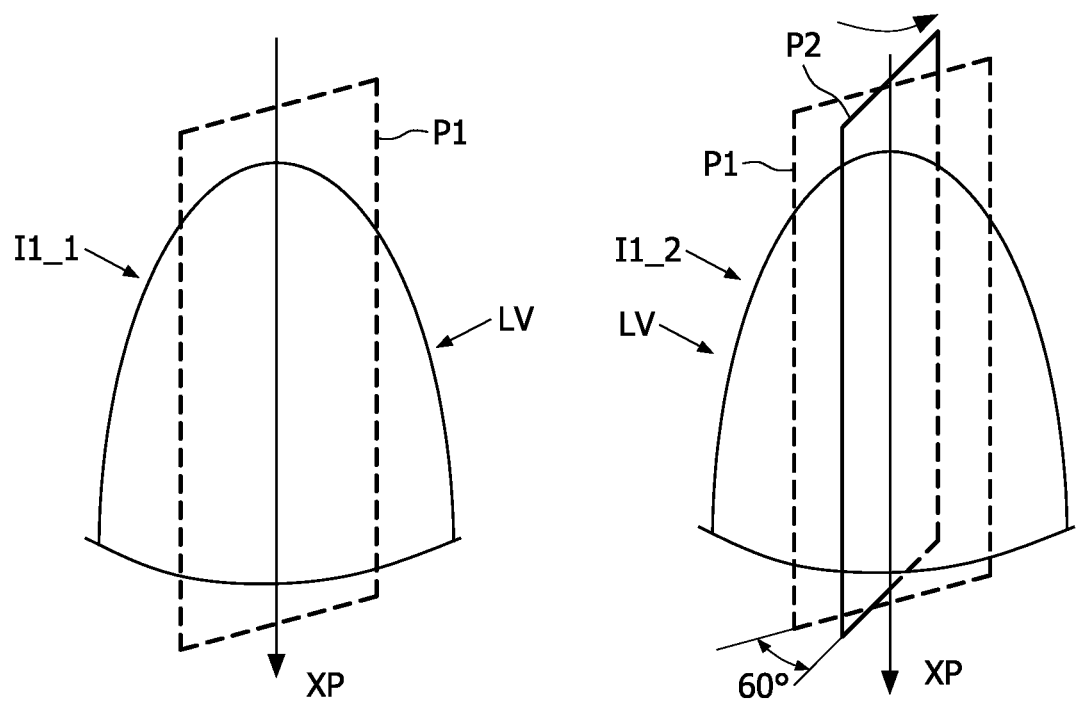
FIG. 13 is a schematic diagram of a sequence of images of the left ventricle of the heart acquired in two different planes by the ultrasound imaging system of FIG. 1.

For example as illustrated in FIG. 13, at least two sequences of images in two different planes P1 and P2 are acquired. It is called a bi-plane mode. A first image I1_1 of the first plane P1 is acquired as illustrated in FIG. 13, which is taken as a baseline, and a second image I1_2 of the second plane P2 shifted from some degrees from the baseline. In a not limited embodiment, the shifting is of 60°.

In a not limited embodiment, three sequences of images are acquired in three different planes P1, P2, P3. The baseline, one sequence shifted from 60° from the baseline and the last one shifted from 120° from the baseline. It allows to have an image of three portions of segments which are in different segments SG of the left ventricle LV.

For example, the first plane P1 will allow to have an image of a first portion which is in the segments 1, 7, 1, 13, 15, 10 and 4, the second plane P2 will allow to have an image of a second portion which is in the segments 2, 8, 14, 17, 16, 11, 5, and the last plane P3 will allow to have an image of a third portion which is in the segments 3, 9, 14, 17, 16, 12, and 6. Hence, all the segments of the left ventricle are covered.

In the 2D acquisition, one acquires these two (or three) sequences simultaneously.

In the 3D acquisition, a volume is acquired and one subsequently acquires two (or three) different sections to obtain these two (or three) sequences.

It is to be noted that this X-plane mode can also be used for a visual assessment about the existence of some displacement difference between two (or three) different portions of segments, displacement such as radial extension. Such large displacements are visible to the naked eye and show that a delay of contraction between two different segments SG exists. If a delay is detected, a region (if 2D images are acquired) or volume (if 3D images are acquired) of interest RI/VI where a delay exists is selected by the user via the user interface M_USER.

Hence the controller CTRL and the means for enabling selection M_SEL make it possible to perform a screening of region(s)/volume(s) of interest RI/VI, in order to look for any asynchronism between different parts of the left ventricle LV quantitatively (by way of different curves, or by way of colorization) but in a not precise way. Of course, alternatively, as described before, a qualitative screening (by visual assessment with or without the help of colorization) may be performed.

3) Determination of a sub-volume S_V1, focused on said selected region/volume of interest RI/VI, via the determination means M_DEF. The position and size of said sub-volume S_V1 on the sequence of images I1 (2D or 3D sequence) can be displayed on the screen SCR for example in dash lines.

The sub-volume S_V1 may be automatically determined and displayed on the screen SCR with its parameters (depth R1, azimuth angle θ1 and elevation angle) in order to cover the region/volume RI/VI of interest.

Figure 14:
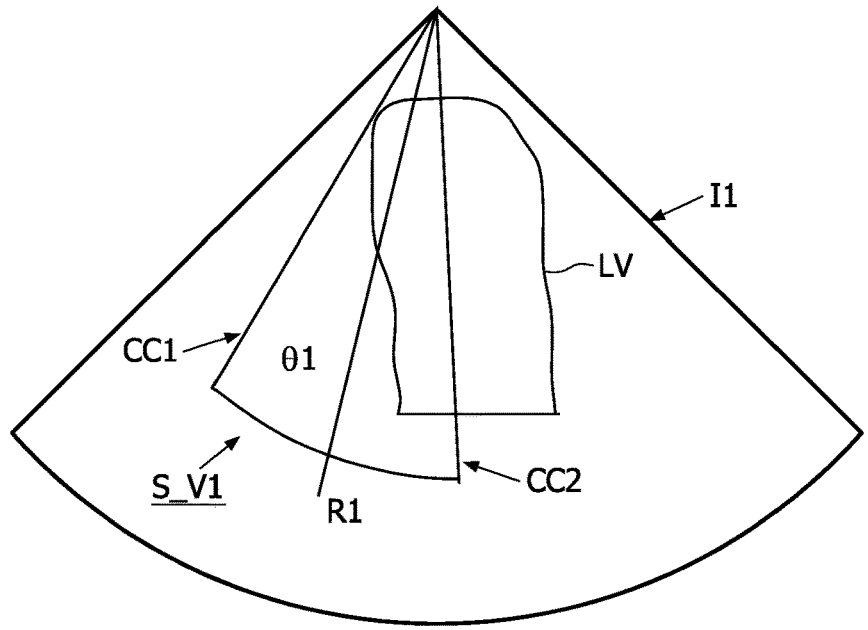
FIG. 14 shows a first sub-volume of a part of the heart acquired via the ultrasound imaging system of FIG. 1.

Then, the user can change manually the position and size of said sub-volume (for example with two cursors CC1, CC2 displayed on the screen SCR as illustrated in FIG. 14) in order to obtain another image rate for example. To this end, the user interface M_USER comprises means in order to give the user this possibility. It is to be noted that the image rate is a function of the size of the sub-volume S_V1 (at a constant density of scan lines).

Of course, alternatively, the user can determine himself manually this sub-volume S_V1 with the two cursors CC1, CC2. If the sequence of images acquired at the first rate IR1 are in 2D, the user can define the elevation angle by viewing a second plane P2 of images for example.

Thus, the user interface M_USER may comprise means which give the user the choice between an automatic and a manual sub-volume determination.

4) Acquisition of the second sequence of ultrasound three-dimensional images I3D_1 of said sub-volume S_V1 at a second image rate IR2. In a not limited embodiment, this second image rate IR2 is higher or equal to 50 Hz. It allows to focus on the region/volume RI/VI with a very good spatial and temporal resolution which lead to a good quality of 3D image.

It is to be noted that the technique of acquiring a 3D image is well-known by the person skilled in the art and therefore will not be described here.

It is to be noted that by acquiring 3D dimensional images at a high image rate IR2, a faster acquisition is possible. For example, when the image rate acquisition is increased up to 80 Hz, one goes four times faster than when the image rate acquisition is of 20 Hz.

It is to be noted that the transducer's array used produces a number of scan lines which are spaced, in a not limited embodiment between 0.5° and 1.5°, from each other. This leads to a good density of scan lines which allows obtaining a good spatial resolution of the 3D ultrasound images and thus a better quality of image.

This 3D sequence I3D_1 of images may be displayed on the screen SCR.

Figure 15:
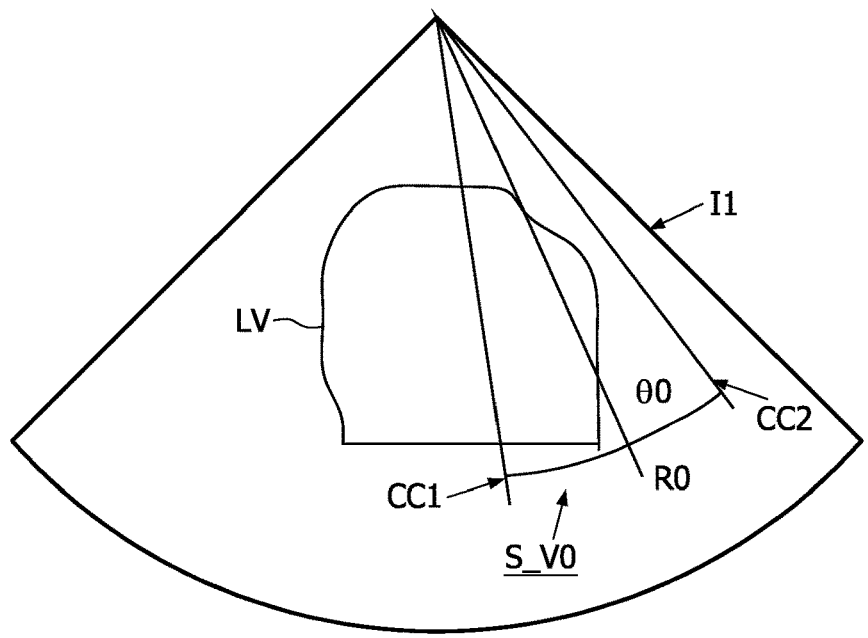
FIG. 15 shows a second sub-volume of a part of the heart acquired via the ultrasound imaging system of FIG. 1.

5) Determination of another sub-volume S_V0 which is taken as a reference as illustrated in FIG. 15 via the determination means M_DEF.

Of course, in the same way as for the first sub-volume S_V1, alternatively, the user can perform himself this operation.

6) Acquisition of the third sequence of 3D images I3D_2 corresponding to said reference sub-volume S_V0. This 3D sequence I3D_2 of images may be displayed on the screen SCR.

7) Comparison of the sub-volume S_V1 with the reference sub-volume S_V0 via the comparator CMP. This comparison can be performed in many different ways. For instance, it is possible to compute displacement curves representing the displacement of the sub-volume S_V1 and the reference sub-volume S_V0 during a cardiac cycle. If these curves are identical, then there is no asynchronism between the sub-volume S_V1 and the reference sub-volume S_V0. If the curves are different, then there may be asynchronism. One may for instance detect a delay TDL between these two curves at a representative time (such as the time of maximum displacement). As it is known in the field of 3D ultrasonic images, and in particular in Cardiac Resynchronisation Therapy, how to compare 2 different volumes, there is no need to describe it further. The main difference between the present invention and the prior art is that this comparison is performed between images acquired at higher image rate than in the prior art, which leads to a much more precise comparison.

The result of the comparison may be displayed on the screen SCR. For instance, the user may be warned that there is a delay TDL between the sub-volume S_V1 and the reference sub-volume S_V0.

Figure 16:
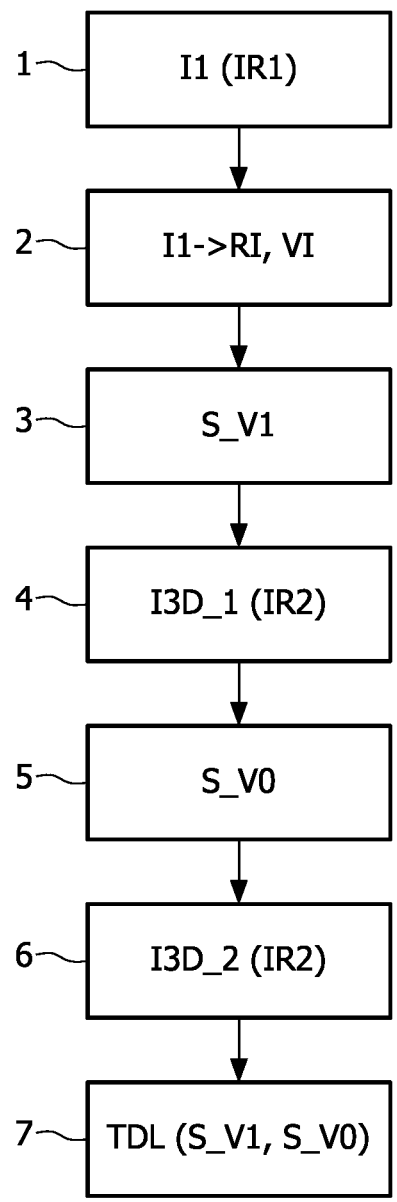
FIG. 16 represents a diagram of an embodiment of a method for ultrasound imaging according to the invention.

As a summary, FIG. 16 illustrates the method for ultrasound imaging according to the invention where one can see the different operations controlled by the system SYS. Of course, some operations may be performed in parallel. For example, the acquisition of the 3D sequence of the sub-volume S_V1 covering the part of interest RI/VI and the acquisition of the 3D sequence of the reference sub-volume S_V0 may be performed in parallel and may both be displayed on the screen SCR of the system SYS.

It is to be noted that such an ultrasound imaging system SYS may be used in a plurality of applications for the heart such as, but not limited to, synchronisation measurements.

The synchronisation measurement allows to detect if a part of the left ventricle is contracting in synchronism with another part of the left ventricle and to detect a potential defect if not. Thanks to the ultrasound imaging system described, one can see if there is a synchronisation or not. Subsequently, one can use a pacemaker to correct this defect of the heart and to stimulate the part of the heart which doesn't work correctly. It is to be noted that there is a synchronism defect of the heart if the delay of contraction between two parts of said heart is around 40 ms. One can understand that with the image rate of the 3D acquisition by means of the system described, one can detect such a defect, which would not be possible with the 3D image acquisition rate of 20 Hz (50 ms between two images) of the prior art.

Hence, the ultrasound imaging system of the present invention that has been described comprises the following advantages:

As seen before, it allows to detect dysfunction between two different parts of the heart with the synchronisation measurement.

Thanks to the 3D acquisition, one can obtain a sequence of images with a significant number of images (superior or equal to 50 images per second) of the part of the heart which can have some problem in order to have a precise view and this with a good resolution (the number of scan lines being kept around a thousand or more). In this case, one have a good field of view as the image rate acquisition and the density of scan lines are satisfying.

Moreover, thanks to the acquisition of the first sequence of images by the ultrasound imaging system described, one can perform some global volume measurement as the first step gives the inner wall of the heart.

One reminds that the global volume measurement consists in measuring the volume of blood within the cavity of the heart. More particularly, the ejection fraction EF, which is the fraction of blood ejected by the ventricle relative to its end-diastolic volume, is computed.

Therefore, EF is calculated from: EF=(SV/EDV)·100 where SV=stroke volume, EDV=end-diastolic volume.

Hence, a good estimates of end-diastolic (EDV) and end-systolic volumes (ESV), and stroke volume (SV=EDV_ESV) is provided.

With the ultrasound imaging system described, one can prevent some heart failure and one can apply the appropriate therapy, for example a cardiac resynchronisation therapy CRT which consists in stimulating the heart's chambers (ventricles plus atriums) to beat simultaneously, so that they are more efficient in pumping blood to the body. The stimulation can take place via a pulse generator and pacing leads (pacemaker), which are placed next to the heart's tissue.

It should be noted that the above-mentioned embodiments illustrate rather than limit the invention, and that those skilled in the art will be capable of designing many alternative embodiments without departing from the scope of the invention as defined by the appended claims.

In the claims, any reference signs placed in parentheses shall not be construed as limiting the claims. The word "comprising" and "comprises", and the like, does not exclude the presence of elements or steps other than those listed in any claim or the specification as a whole. The singular reference of an element does not exclude the plural reference of such elements and vice-versa.

The invention may be implemented by means of hardware comprising several distinct elements, and by means of a suitably programmed computer. In a device claim enumerating several means, several of these means may be embodied by one and the same item of hardware. The mere fact that certain measures are recited in mutually different dependent claims does not indicate that a combination of these measures cannot be used to advantage.

The invention claimed is:

1. An ultrasound image acquisition system, comprising:
an ultrasonic probe configured to image an organ, the ultrasonic probe including a transducer array; and
a computer in communication with the ultrasonic probe, the computer comprising:
  a controller for controlling the transducer array to:
  acquire at a first image rate (IR1) of a first sequence of ultrasound images (I1) of the organ (LV),
  after acquisition at the first image rate (IR1) of the first sequence of ultrasound images (I1) of the organ (LV), acquire at a second image rate (IR2) of a second sequence of ultrasound three-dimensional images (I3D_1) of a sub-volume (S_V1) by focusing on a selected part of interest (RI/VI) associated with the organ in said first sequence (I1), wherein focusing comprises the controller adjusting at least one of a spatial or a temporal resolution of the transducer array to acquire a 3D image of the selected part of interest with an increased image resolution relative to the first sequence of ultrasound images, wherein the second imaging rate (IR2) is different from the first imaging rate (IR1),
  after acquisition at the first image rate (IR1) of the first sequence of ultrasound images (I1) of the organ (LV), acquire at the second image rate (IR2) of a third sequence of ultrasound three-dimensional images (I3D_2) of a reference subvolume (S_V0); and
an image comparator module in communication with the controller, the image comparator module for comparing said second and third sequences of three dimensional images (I3D_1, I3D_2),
wherein the image comparator module is configured to:
determine a first plurality of displacement curves representative of a displacement of the subvolume (S_V1);
determine a second plurality of displacement curves representative of a displacement of the reference subvolume (S_V0); and
identify asynchronism when a delay between the first plurality of displacement curves and the second plurality of displacement curves is detected;
wherein the controller is configured to control the transducer array to acquire, in parallel, the second and third sequences of images.

2. An ultrasound image acquisition system as claimed in claim 1, wherein the second image rate (IR2) is equal to 50 Hz.

3. An ultrasound image acquisition system as claimed in claim 1, wherein the images (I1) acquired at the first image rate (IR1) are in two-dimensions.

4. An ultrasound image acquisition system as claimed in claim 3, wherein the first image rate (IR1) is equal to 40 Hz.

5. An ultrasound image acquisition system as claimed in claim 1, wherein the images (I1) acquired at the first image rate (IR1) are in three-dimensions.

6. An ultrasound image acquisition system as claimed in claim 1, wherein the controller is configured to automatically select said part of interest (RI, VI) in said first sequence of ultrasound images (I1).

7. An ultrasound image acquisition system as claimed in claim 6, wherein the selection of the part of interest (RI/VI) is based upon velocity information of some parts of the organ.

8. An ultrasound image acquisition system as claimed in claim 7, wherein the selection is based upon a COLOR KINESIS method (CK).

9. An ultrasound image acquisition system as claimed in claim 1, wherein the controller (CTRL) is arranged to control acquisition of a plurality of sequences of images in a plurality of planes (P1, P2, P3) during a same time period.

10. An ultrasound image acquisition system as claimed in claim 1, further comprising a screen configured to display a warning when the delay is detected.

11. A method for ultrasound imaging, comprising the steps of:
positioning an ultrasonic probe with respect to a body of a patient to image an organ, the ultrasonic probe including a transducer array;
acquiring, by a controller in communication with the ultrasonic probe and operable to control the transducer array, at a first image rate (IR1) a first sequence of ultrasound images (I1) of the organ (LV);
after acquiring the first sequence of ultrasound images (I1) of the organ (LV) at the first image rate (IR1), acquiring, by the controller, at a second image rate (IR2) a second sequence at a second image rate (IR2) of ultrasound three-dimensional images (I3D_I1) of a subvolume (S_V1) by focusing on a selected part of interest (RI/VI) associated with the organ in said first sequence (I1), wherein focusing comprises adjusting at least one of a spatial or a temporal resolution of the ultrasonic probe to acquire a 3D image of the selected part of interest with an increased image resolution relative to the first sequence of ultrasound images, wherein the second image rate is different from the first image rate;
after acquiring the first sequence of ultrasound images (I1) of the organ (LV) at the first image rate (IR1), acquiring, by the controller and in parallel with acquiring the second sequence, at the second image rate (IR2) a third sequence of ultrasound three-dimensional images (I3D_2) of a reference sub-volume (S_V0); and
comparing, by a comparator module in communication with the controller, said second and third sequences of three-dimensional images (I3D_1, I3D_2)
wherein the image comparator module is configured to:
determine a first plurality of displacement curves representative of a displacement of the subvolume (S_V1);
determine a second plurality of displacement curves representative of a displacement of the reference subvolume (S_V0); and
identify asynchronism when a delay between the first plurality of displacement curves and the second plurality of displacement curves is detected.

12. A method for ultrasound imaging as claimed in claim 11, further comprising selecting the part of interest (RI/VI).

13. A method for ultrasound imaging as claimed in claim 12, wherein selecting comprises: acquiring velocity information of some parts of the organ, colorizing the velocity information, and visually assessing a part of the organ whose color is not uniform compared to other parts of the organ.

14. A method for ultrasound imaging as claimed in claim 12, wherein selecting comprises: acquiring velocity curves (CV1, CV2) associated to some parts of the organ, and visually assessing a delay (TD) between these velocity curves (CV1, CV2) at a representative time (TPV).

15. An ultrasound image acquisition system as claimed in claim 1, wherein the second image rate (IR2) is greater than the first image rate (IR1).

16. An ultrasound image acquisition system as claimed in claim 1, wherein the second image rate (IR2) allows detection of a synchronism defect of a heart.

* * * * *